United States Patent [19]

Clausen et al.

[11] Patent Number: 4,984,972
[45] Date of Patent: Jan. 15, 1991

[54] CENTRIFUGAL BLOOD PUMP

[75] Inventors: Earl W. Clausen, Eden Prairie; Lloyd C. Hubbard, Deephaven, both of Minn.

[73] Assignee: Minnesota Mining and Manufacturing Co., St. Paul, Minn.

[21] Appl. No.: 426,102

[22] Filed: Oct. 24, 1989

[51] Int. Cl.⁵ .................... F04D 7/02; F04D 25/06
[52] U.S. Cl. ........................... 417/420; 415/900
[58] Field of Search ..................... 417/420; 415/900

[56] References Cited

U.S. PATENT DOCUMENTS

| | | | |
|---|---|---|---|
| 3,354,833 | 11/1967 | Laing | 417/420 X |
| 3,411,450 | 11/1968 | Clifton | 417/420 |
| 3,575,536 | 4/1971 | Jacobs | 417/420 |
| 3,645,650 | 2/1972 | Laing . | |
| 3,647,324 | 3/1972 | Rafferty et al. . | |
| 3,762,839 | 10/1973 | Laing . | |
| 3,771,910 | 11/1973 | Laing | 417/420 |
| 3,838,947 | 10/1974 | Laing | 417/420 X |
| 3,864,055 | 2/1975 | Kletschka et al. . | |
| 4,352,646 | 10/1982 | Laing | 417/420 |
| 4,507,048 | 3/1986 | Belenger et al. | 415/900 X |
| 4,589,822 | 5/1986 | Clausen et al. | 415/900 X |
| 4,606,698 | 8/1986 | Clausen et al. | 415/900 X |
| 4,643,641 | 2/1987 | Clausen et al. | 415/900 X |
| 4,688,998 | 8/1987 | Olsen et al. . | |
| 4,898,518 | 2/1990 | Hubbard et al. | 415/900 X |

FOREIGN PATENT DOCUMENTS

| | | | |
|---|---|---|---|
| 2048286 | 11/1971 | Fed. Rep. of Germany | 417/420 |
| 1728462 | 1/1973 | Fed. Rep. of Germany | 417/420 |
| 43-17206 | 7/1968 | Japan | 417/420 |

Primary Examiner—Gerald A. Michalsky
Attorney, Agent, or Firm—Kinney & Lange

[57] ABSTRACT

A disposable pumping unit has a pump housing which encloses a pumping chamber therein. The pump housing includes an inlet and an outlet communicating with the pumping chamber. A stator is connected to the pump housing and has a distal end which extends into the pumping chamber. The stator defines a central axis. A bearing is supported at the distal end of the stator and is aligned with the central axis. Positioned within the pumping chamber is a rotator supported on the bearing for rotation about the central axis. At least one magnet is carried by the rotator.

45 Claims, 5 Drawing Sheets

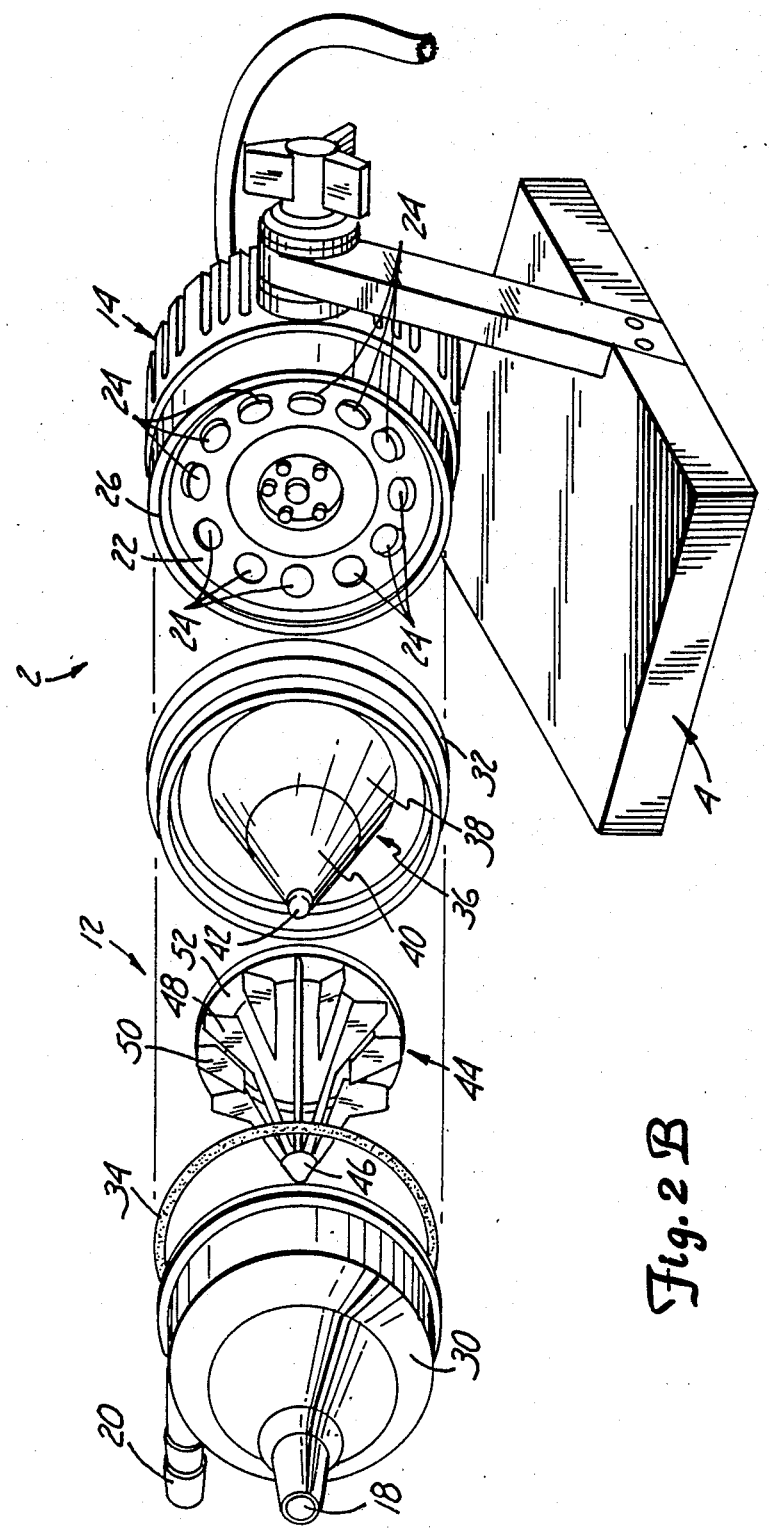

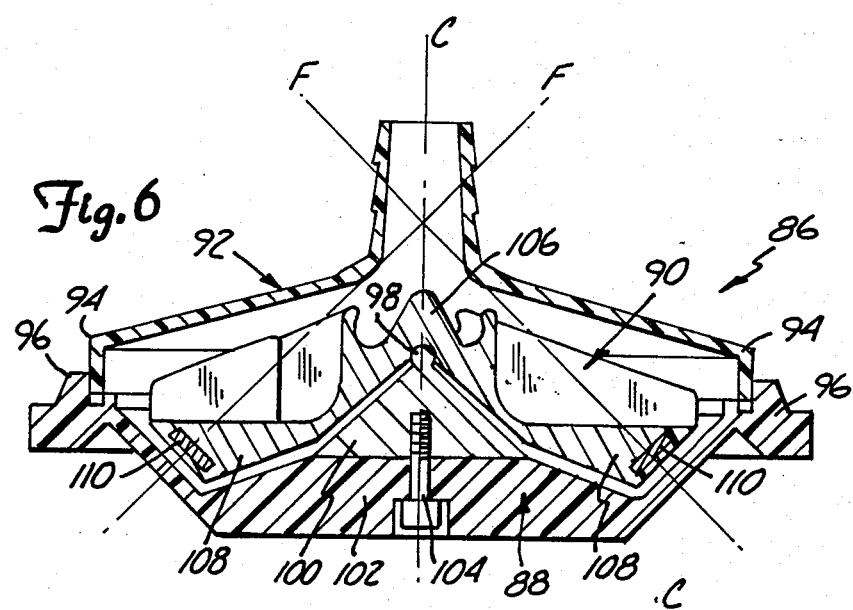
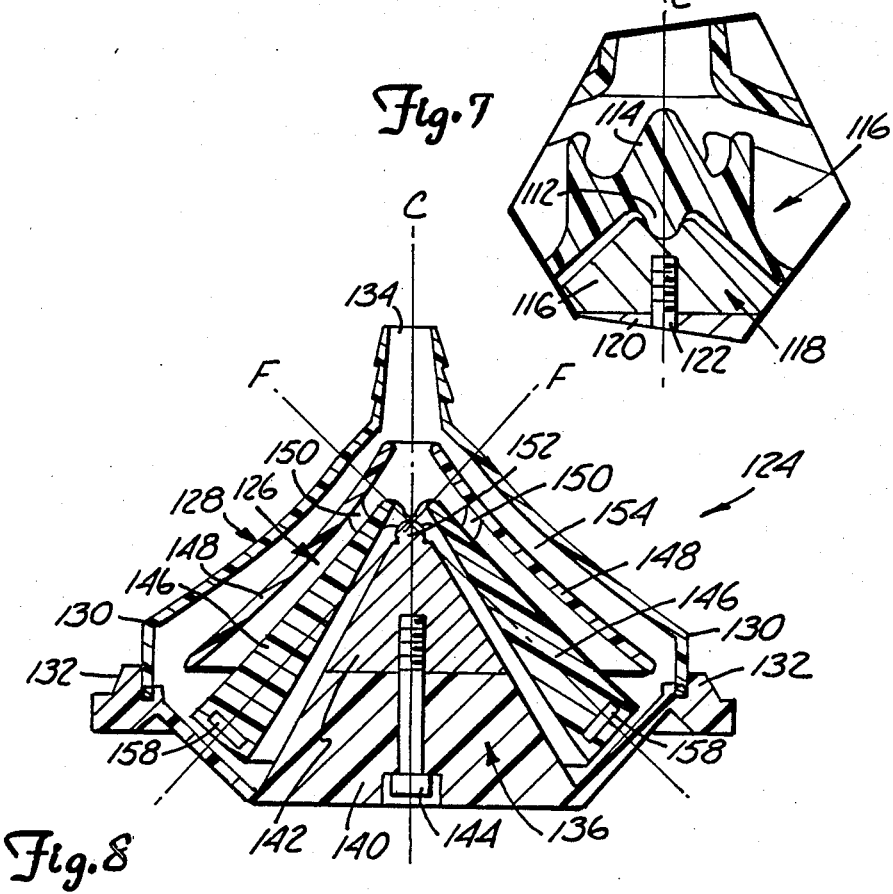

CENTRIFUGAL BLOOD PUMP

BACKGROUND OF THE INVENTION

1. Field of the Invention

The present invention is related to centrifugal blood pumps.

2. Description of the Prior Art

Centrifugal pumps have been used for many years to pump a wide variety of different fluid materials. In general, a centrifugal pump includes a pump housing enclosing a pumping chamber therein, an inlet aligned with a rotational axis of the pump, an outlet adjacent to the periphery of the pumping chamber, a rotator mounted within the pumping chamber for rotation about the axis, and a drive source communicating with the rotator. The rotator and drive source have several possible configurations. In one configuration, the rotator is mounted on a drive shaft which extends outside the pumping chamber to a rotational drive source. In another configuration, the pump housing encloses two chambers, one containing a magnetic rotor and the other containing the pumping chamber and rotator. The rotator and rotor are connected by a drive shaft. Seals are used to isolate the two chambers. A magnetic drive source communicates with the rotor to rotate the rotator within the pumping chamber. In still another configuration, the rotator is suspended within the pumping chamber by a magnetic means formed within the pump housing. Examples of these centrifugal pumps are shown in the following U.S. Patents: Kletschka et al U.S. Pat. No. 3,864,055; Rafferty et al U.S. Pat. No. 3,647,324; and Olsen et al U.S. Pat. No. 4,688,998.

In recent years, centrifugal pumps have been used extensively for pumping blood during open heart surgery. The pumping of blood requires great care to avoid any damage to the red corpuscles, or any of the other constituents of blood. Any practical blood pump useful as part of heart/lung bypass equipment during open heart surgery must deliver the requisite flow volumes under pressure, without damaging the blood being pumped.

In a prior art centrifugal pump, and in particular in a centrifugal pump for pumping liquids such as blood, a fluid tight seal between the drive shaft and the housing is an important factor in the performance of the pump. Friction at the seal produces heat which, if not dissipated, can damage both the components of the pump and the blood being pumped. Also, the rotation of the rotator can lead to generation of an air bubble surrounding the shaft. This air bubble tends to seek the smallest shaft diameter, which typically is adjacent the drive shaft seal. In some of the prior art pumps, the area adjacent the drive shaft seal has also been a relatively stagnant or low flow area in terms of fluid flow within the pumping chamber. The air bubble tends to insulate the seal from the flow of the fluid within the pumping chamber, thus decreasing the dissipation of heat generated by friction at the seal surface.

It is often the case that blood pumps are used only once. After a single use, the portions of the pump which contact the blood must either be disposed of or its constituent parts must be sterilized. A centrifugal blood pump comprising a minimal number of parts is desirable to reduce costs and improve reliability.

SUMMARY OF INVENTION

The present invention is an improved centrifugal pump which includes a disposable pumping unit. The pumping unit includes a pump housing enclosing a pumping chamber therein. The pump housing has an inlet and an outlet communicating with the pumping chamber. A stator is connected to the pump housing and has a distal end extending into the pumping chamber. A bearing is supported at a distal end of the stator and is aligned with a central axis defined by the stator. Positioned within the pumping chamber is a rotator supported at a hub by the bearing for rotation about the central axis. At least one magnet is carried by the rotator.

In one preferred embodiment, the bearing is a ball-shaped pivot bearing made, for example, from hard-coated aluminum to provide sufficient heat dissipation. The rotator carries an annular magnetic ring about its circumference. The magnetic ring has a plurality of magnetic poles and is positioned such that the magnetic lines of force are substantially directed toward the bearing and the central axis. The resulting unbalanced forces on the rotator hub are generally parallel to the central axis in a downward direction from the hub to the bearing, therefore stabilizing the rotation of the rotator about the central axis.

The centrifugal pump preferably includes a magnetic drive device releasably connected to the disposable pumping unit. The magnetic drive device includes a rotor having a plurality of drive magnets spaced annularly about its circumference. The drive magnets are positioned such that their magnetic lines of force align with and are generally parallel to the magnetic lines of force of the magnetic ring carried by the rotator within the pumping chamber. The drive magnets communicate with the magnetic ring carried by the rotator, and thereby rotate the rotator within the pumping chamber as the rotor of the magnetic drive device is rotated.

BRIEF DESCRIPTION OF THE DRAWINGS

FIG. 2B is an exploded view of the centrifugal blood pump of FIGS. 1 and 2A.

FIG. 6 is an alternate embodiment having a low profile and stator arrangement similar to the one shown in FIG. 4.

FIG. 7 is a fragmentary detail of an alternate bearing arrangement.

FIG. 8 is a partial sectional view of an embodiment with an alternate rotator arrangement.

DETAILED DESCRIPTION OF THE PREFERRED EMBODIMENTS

FIGS. 1-4 show one embodiment of the centrifugal blood pump of the present invention. FIGS. 5-8 illustrate alternate embodiments.

Figure 1:
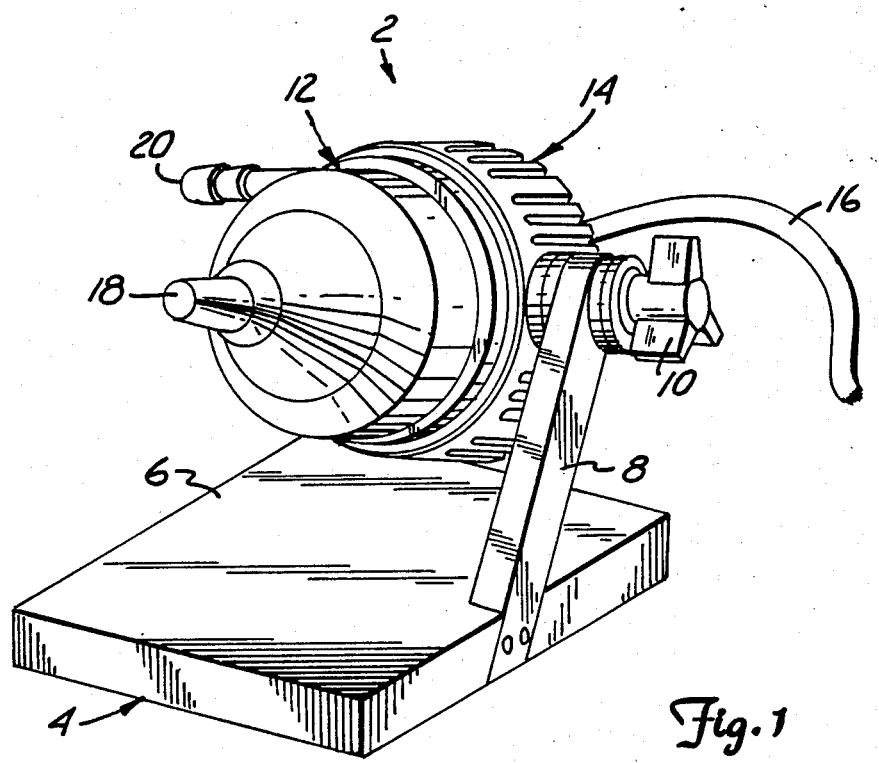
FIG. 1 is a perspective view of a centrifugal blood pump of the present invention.

FIG. 1 shows a perspective view of a centrifugal blood pump 2. Pump 2 is mounted on stand 4 (formed by base 6, support arm 8 and locking nut 10) and comprises a disposable pumping unit 12 and a magnetic drive device 14. Disposable pumping unit 12 is releasably connected to magnetic drive device 14. Electric cord 16 connects magnetic drive device 14 to an electric power source (not shown) and thereby provides electric excitation to magnetic drive device 14. During pump operation, blood enters disposable pumping unit 12 through inlet 18 and is pumped out through outlet 20.

Figure 2A:
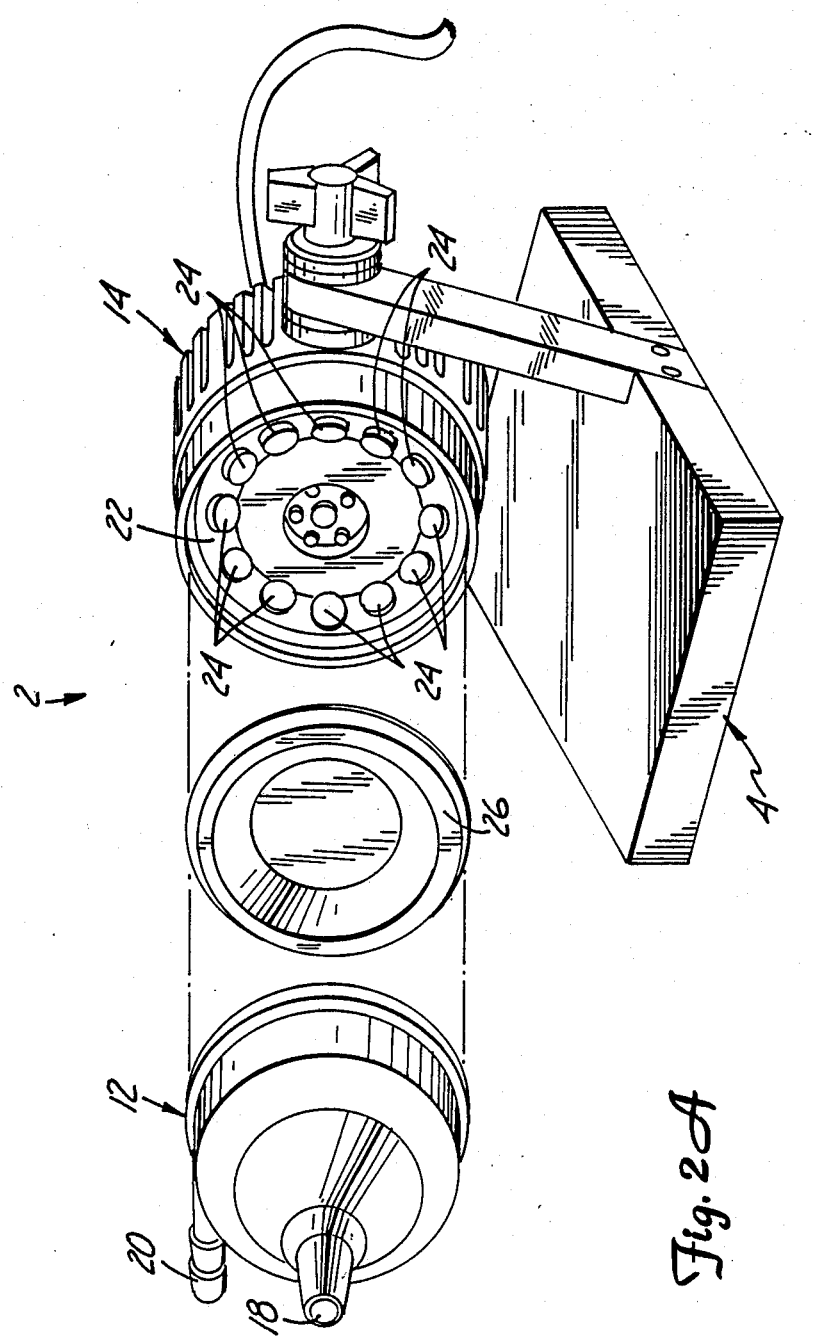
FIG. 2A is an exploded view of the pump of FIG. 1 showing the disposable pumping unit detached from the magnetic drive device.

FIGS. 2A and 2B are exploded views of the centrifugal pump shown in FIG. 1. FIG. 2A shows the centrifugal pump of FIG. 1 with disposable pumping unit 12 detached from magnetic drive device 14. Magnetic drive device 14 includes a rotor 22 having a plurality of circumferentially spaced drive magnets 24. Protective plate 26 is positioned adjacent the drive magnets 24 and is supported by the face of magnetic drive device 14. Protective plate 26 isolates rotor 22 from foreign objects and contaminants which could impede the operation of magnetic drive device 14.

Figure 4:
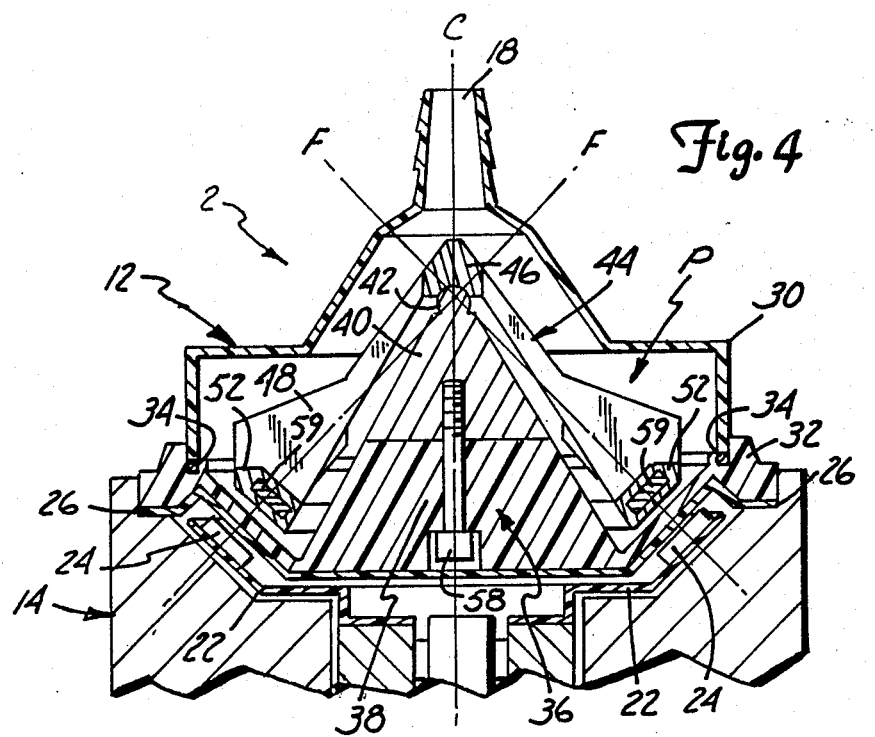
FIG. 4 is a transverse section of the pump taken along line 4—4 of FIG. 3 and includes the magnetic drive device of FIGS. 1, 2A and 2B.

As shown in FIG. 2B, the disposable pumping unit 12 comprises a pump housing (formed by housing cap 30 and housing base 32) enclosing a pumping chamber P therein (shown in FIG. 4). Housing cap 30 includes inlet 18 and outlet 20 and is preferably transparent so that operation of pump 2 can be visually monitored. The inlet 18 is aligned with a central axis C and the outlet 20 is positioned at the periphery of housing cap 30. An annular seal 34 is placed between housing cap 30 and housing base 32 to provide a fluid-tight seal for the pumping chamber P.

Disposable pumping unit 12 also includes a stator 36 having a proximal end and a distal end. The proximal end is secured to housing base 32 and the distal end extends into the pumping chamber P. Stator 36 defines the central axis C and is generally conical shaped to reduce the stagnation of fluid near the central axis C. Stator 36 comprises two sections: a proximal section 38 and a distal section 40. Proximal section 38 is shaped as a frustal cone which can either be secured to or formed integral with housing base 32. Distal section 40 is cone shaped and secured to proximal section. Stator 36, in an alternate embodiment, can be formed as one piece.

A bearing 42 is formed integral with the distal end of stator 36. Bearing 42, alternatively, can be formed separately and then secured to the distal end of stator 36. Bearing 42 is shown as a ball-shaped pivot bearing but those skilled in the art can replace bearing 42 with any one of a number of bearing types. Bearing 42 is generally aligned with the central axis C. Bearing 42 is preferably made from a material having sufficient heat dissipation qualities, such as hard-coated aluminum. Distal section 40 of stator 36 is also preferably made from material having good heat dissipation qualities. Heat dissipation is very important near bearing 42 to protect both bearing 42 and the blood being pumped through the pumping chamber P.

A rotator 44 is positioned within the pumping chamber and is supported on bearing 42 for rotation about the central axis C. In this embodiment, the rotator 44 is configured as an impeller which is generally conical shaped. Rotator 44 has a hub 46 aligned with the central axis C for engagement with bearing 42. Rotator 44 includes long blades 48, short blades 50, and circular flange 52. Long blades 48 are attached at their inner ends to rotator hub 46. Flange 52 is attached to and is supported by long blades 48. Short blades 50 are supported by flange 52. In the particular embodiment shown in FIGS. 2A and 2B, long and short blades 48 and 50 are alternately spaced about the circumference of rotator 44. Large diameter impellers require a greater number of blades in order to achieve pumping efficiency. By use of short blades 50 supported by flange 52, rotator 44 achieves pumping efficiency while retaining a small hub diameter, since only long blades 48 are attached to hub 46. Rotator 44 carries magnetic means 59 (shown in FIG. 4) on or within flange 52 such that the magnetic means is axially displaced from bearing 42.

Magnetic drive device 14 includes drive magnets 24 which communicate with magnetic means 59 carried by rotator 44 on flange 52 to rotate the rotator 44 within the pumping chamber P. The magnetic means 59 carried by rotator 44 and the drive magnets 24 carried by rotor 22 must have enough attraction strength to achieve the desired operation of centrifugal blood pump 2. It is preferable to have drive magnets 24 be stronger than magnetic means 59 carried by rotator 44 so less expensive magnets are used within disposable pumping unit 12.

Figure 3:
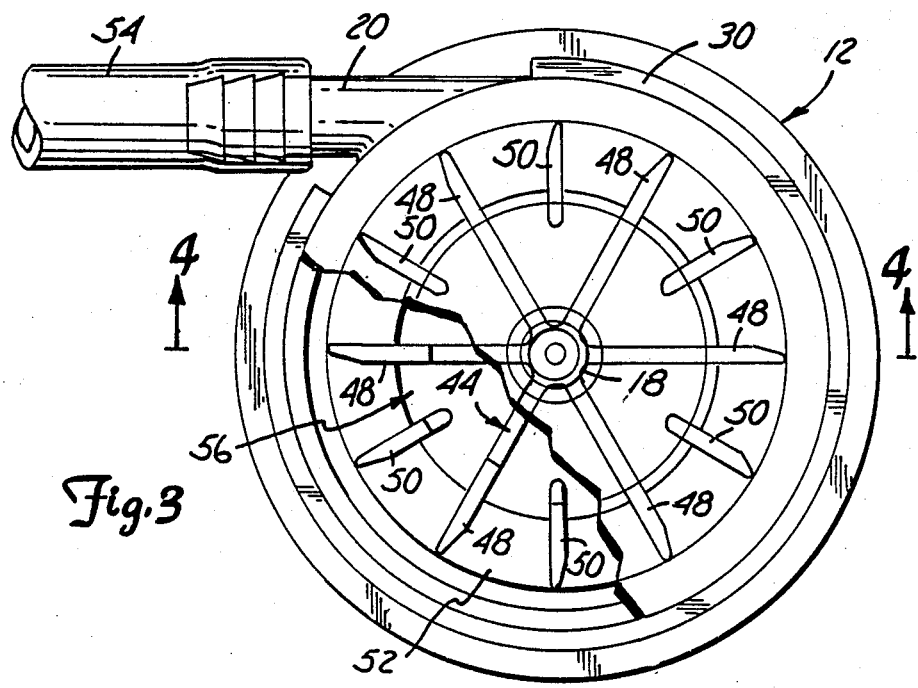
FIG. 3 is a plan view of the pumping unit of FIGS. 1, 2A and 2B removed from the magnetic drive means.

FIG. 3 is a plan view of disposable pumping unit 12 shown in FIGS. 1, 2A and 2B. The transparent housing cap 30 is shown with inlet 18 positioned on the central axis C and outlet 20 positioned at the periphery. A tube 54 can be fitted to housing cap 30 at outlet 20 for transferring fluid from pumping chamber 56 to a destination. Rotator 44 is shown with long blades 48, short blades 50 and flange 52.

FIG. 4 is a transverse section of centrifugal pump 2 shown in FIGS. 1, 2A and 2B. Centrifugal pump 2 comprises disposable pumping unit 12 and magnetic drive device 14. Disposable pumping unit 12 includes housing cap 30 (with inlet 18), housing base 32, annular seal 34, stator 36, screw 58, and rotator 44. Stator 36 comprises proximal section 38 and distal section 40 which are secured together by screw 58. In this embodiment, proximal section 38 is formed integral with housing base 32. Bearing 42 is formed integral with the distal end of stator 36 and supports hub 46 of rotator 44. Rotator 44 is shown carrying magnetic means 59 on flange 52. Magnetic means 59 is a magnetic ring having a plurality of magnetic poles (not shown) and is commercially available. Alternatively, a plurality of circumferentially spaced magnets can be carried by flange 52. Magnetic drive device 14 comprises protective plate 26 and drive magnets 24 carried by rotor 22.

FIG. 4 also shows the positional relationship between magnetic means 59 carried by rotator 44 and drive magnets 24 carried by rotor 22. The magnetic lines of force F of magnetic means 59 are substantially directed toward bearing 42 and central axis C. Drive magnets 24 are positioned such that their magnetic lines of force F generally align with and are parallel to the magnetic lines of force F generated by magnetic means 59 carried by rotator 44. The resulting unbalanced forces on rotator 44 generally align with the central axis C and are in a downward direction from rotator hub 46 toward bearing 42. With this magnet orientation, the balanced forces stabilize rotation of rotator 44 about central axis C and hold rotator 44 against bearing 42.

Figure 5:
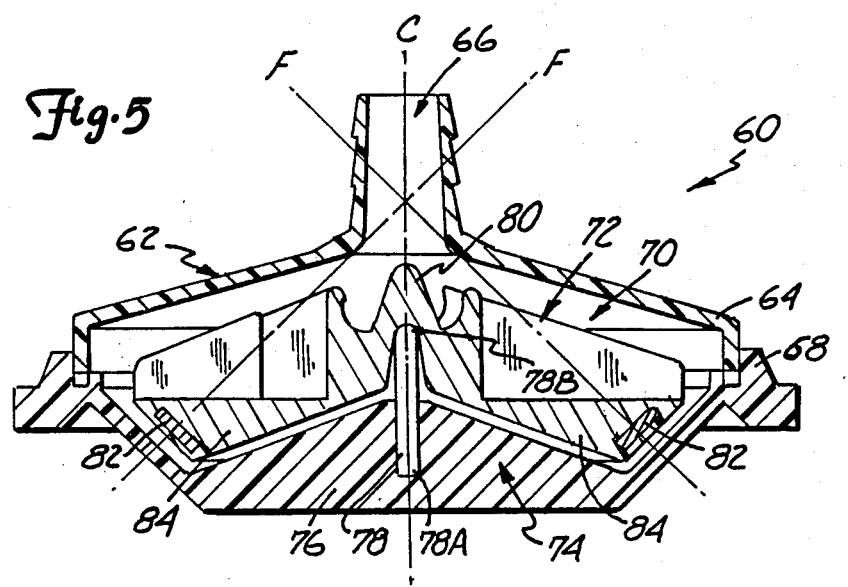
FIG. 5 is a view similar to FIG. 4 of an alternate embodiment having a low profile and an alternate stator arrangement.

FIG. 5 shows an alternate embodiment of a disposable pumping unit 60 having a lower profile than shown in FIG. 4. This embodiment includes pump housing 62, housing cap 64 with inlet 66, housing base 68, pumping chamber 70, rotator 72, and stator 74. The outlet of housing 62 is not shown in FIG. 5, but is positioned similarly to outlet 20 shown in FIG. 1. FIG. 5 not only shows a low profile pumping unit, but also shows stator 74 as an alternate arrangement to stator 36 shown in FIG. 4. Stator 74 comprises a stator base 76 (formed integral with the housing base 68) and a spindle 78, which generally replace bearing 42 and distal section 40 of stator 36. Spindle 78 has first and second opposite ends 78A and 78B. The first end 78A is secured to stator base 76 of stator 74; and the second end 78B extends into pumping chamber 70 and is rounded for use as a bearing. Rotator 72 is similar to rotator 44 described in FIG. 4 but it too has a lower profile. Rotator 72 has a different hub configuration 80 to accommodate the lower profile without sacrificing rotator blade area. Hub 80 is preferably made from hard-coated aluminum or similar heat dissipating material. Rotator 72 carries magnetic means 82 on flange 84 such that the magnetic lines of force F are generally directed toward the bearing at the second end 78B of spindle 78 and the central axis C so that rotation of rotator 72 is stabilized about the central axis C. The lower profile pumping unit 60 reduces the volume of pumping chamber 70 while maintaining pumping efficiency. This reduces the amount of blood necessary to prime the pump near the start of operation.

FIG. 6 shows another low profile disposable pumping unit embodiment 86. Pumping unit 86 comprises stator 88, rotator 90, and pump housing 92. Pump housing 92 includes housing cap 94 and housing base 96. A ball-shaped pivot bearing 98 is used instead of the spindle 78 of FIG. 5. Housing base 68 and stator 74 of FIG. 5 have been replaced with housing base 96 and stator 88. Stator 88 has a similar configuration to stator 36 shown in FIG. 4 but has a lower profile. Stator 88 comprises distal section 100, proximal section 102, and screw 104. Stator 88 defines central axis C. Rotator 90 is similar to rotator 72 illustrated in FIG. 5 and includes hub 106, flange 108, and magnetic means 110. Magnetic means 110 creates magnetic lines of force F. In this embodiment, the ball-shaped pivot bearing 98 is formed integral with distal section 100 of stator 88 and is hard-coated aluminum.

The pumping unit 86 in FIG. 6 is shown with an alternate bearing arrangement in the partial sectional view of FIG. 7. Bearing 112 is formed integral with hub 114 of rotator 116. Bearing 112 now rests on distal section 116 of stator 118 for rotation about the central axis C. Distal section 116 is secured to proximal section 120 by screw 122. Bearing 112 can also be formed as a separate element and secured to hub 114 (not shown). The bearing arrangement shown in FIG. 7 can be used in any of the other embodiments shown in the figures.

FIG. 8 shows an alternate embodiment of a disposable pumping unit 124 having an alternate rotator configuration 126. Pumping unit 124 includes pump housing 128, housing cap 130, housing base 132, inlet 134, an outlet (not shown) located at the periphery of housing 128, stator 136, and rotator 126. Stator 136 is similar to stator 36 in FIG. 4 and comprises a proximal section 140, a distal section 142, and a screw 144. Rotator 126 comprises first and second concentric rotator cones 146 and 148 secured together with a plurality of struts 150. The first rotator cone 146 is supported by bearing 152 for rotation of the first and the second rotator cones 146 and 148 about central axis C. First and second cones 146 and 148 each have an opening at the central axis C allowing fluid entering pumping chamber 154 through inlet 134 to increase heat dissipation by lubricating bearing 152. This fluid flow path also limits the stagnation of fluid near the wall of stator 136. The first rotator cone 146 carries magnetic means 158 about its circumference and is oriented such that the magnetic lines of force F are substantially directed toward the bearing 152 and the central axis C.

The present invention provides a centrifugal blood pump having a minimal number of parts requiring disposal or sterilization. The drive shaft seals of prior art centrifugal blood pumps have been eliminated, which increases reliability of the present invention. Reliability is further increased by positioning the bearing, as shown in FIG. 4, near the inlet. This increases blood flow near the bearing and thereby reduces heat build-up on the bearing and on the blood near the surface of the bearing. Heat damage to the blood being pumped is therefore also reduced.

The reduced parts count of the disposable pumping unit along with its simplistic design lowers the relative cost of centrifugal blood pumps with respect to the prior art.

Although the present invention has been described with reference to preferred embodiments, workers skilled in the art will recognize that changes may be made in form and detail without departing from the spirit and scope of the invention.

We claim:

1. A disposable pumping unit adapted to pump biological fluid such as blood, the pumping unit comprising:
    a pump housing having a pumping chamber therein, and having an inlet and an outlet communicating with the pumping chamber;
    a stator having a proximal end and a distal end with the proximal end connected to the pump housing and the distal end extending into the pumping chamber, the stator defining a central axis;
    a bearing supported at the distal end of the stator and aligned with the central axis;
    a rotator positioned within the pumping chamber and supported on the bearing for rotation about the central axis, the rotator having a hub and a plurality of openings configured to expose the bearing to the fluid; and
    magnetic means carried by the rotator within the pumping chamber.

2. The pumping unit of claim 1 wherein the pump housing comprises:
    a housing cap having the inlet generally aligned with the central axis for routing fluid into the pumping chamber;
    a housing base secured to the housing cap thereby enclosing the pumping chamber therein; and
    an annular fluid-tight seal between the housing cap and base.

3. The pumping unit of claim 2 wherein the stator is conical-shaped with the proximal end having a larger radius than the distal end, and wherein the proximal end is secured to the housing base.

4. The pumping unit of claim 1 wherein the stator is conical-shaped having a maximum and a minimum radial dimension, with the proximal end having the maximum radial dimension and the distal end having the minimum radial dimension.

5. The pumping unit in claim 4 wherein the stator comprises a proximal section and a distal section, the proximal section constructed out of a polymer material, the distal section constructed out of hardcoated aluminum.

6. The pumping unit of claim 1 wherein the stator comprises:
   a stator base shaped as a frustal cone with a trapezoidal cross-section along the central axis, the stator base having a maximum radial dimension and a minimum radial dimension, the maximum radial dimension defining the proximal end of the stator; and
   a spindle having first and second opposite ends aligned with the central axis, the first end attached to the minimum radial dimension of the lower section of the stator and the second end defining the distal end of the stator.

7. The pumping unit of claim 6 wherein the bearing is formed integral with the second end of the spindle.

8. The pumping unit of claim 1 wherein the bearing is a ball-shaped pivot bearing.

9. The pumping unit of claim 8 wherein the pivot bearing is hardcoated aluminum.

10. The pumping unit of claim 1 wherein the bearing is fixed to the distal end of the stator.

11. The pumping unit of claim 1 wherein the bearing is formed integral with the distal end of the stator.

12. The pumping unit of claim 1 wherein the bearing is fixed to the hub of the rotator at the central axis.

13. The pumping unit of claim 1 wherein the bearing is formed integral with the rotator at the central axis.

14. The pumping unit of claim 1 wherein the rotator is a generally conical-shaped impeller with a maximum radial end adjacent to the proximal end of the stator and a minimum radial end supported by the bearing.

15. The pumping unit of claim 1 wherein the rotator comprises a plurality of concentric cone-shaped rotators with maximal radial ends adjacent to the proximal end of the stator and with minimal radial ends supported by the bearing.

16. The pumping unit of claim 1 wherein the magnetic means comprises an annular magnetic ring having a plurality of magnetic poles.

17. The pumping unit of claim 1 wherein the magnetic means comprises a plurality of circumferentially spaced magnets.

18. The pumping unit of claim 1 wherein the magnetic means are positioned such that the magnetic lines of force are substantially directed toward the bearing and the central axis.

19. A centrifugal pump adapted to pump biological fluid such as blood, the pump comprising:
   a pump housing having a pumping chamber therein, and having an inlet and an outlet communicating with the pumping chamber;
   a stator having a proximal end and a distal end with the proximal end connected to the pump housing and the distal end extending into the pumping chamber, the stator defining a central axis;
   a bearing supported at the distal end of the stator and being aligned with the central axis;
   a rotator positioned within the pumping chamber and supported on the bearing for rotation about the central axis, the rotator having a hub and a plurality of openings configured to expose the bearing to the fluid;
   magnetic means carried by the rotator; and
   magnetic drive means for releasable connection to the pump housing to communicate with the magnetic means carried by the rotator and thereby to rotate the rotator within the pumping chamber.

20. The centrifugal pump of claim 19 wherein the pump housing comprises:
   a housing cap having an inlet generally aligned with the central axis for routing fluid into the pumping chamber;
   a housing base secured to the housing cap thereby enclosing the pumping chamber therein; and
   an annular fluid-tight seal between the housing cap and base.

21. The centrifugal pump of claim 20 wherein the stator is conical-shaped with a maximum radius at the proximal end and a minimum radius at the distal end, and having the proximal end secured to the housing base.

22. The centrifugal pump of claim 19 wherein the stator is conical-shaped having a maximum and a minimum radial dimension with the proximal end having the maximum radial dimension and the distal end having the minimum radial dimension.

23. The centrifugal pump in claim 22 wherein the stator comprises a proximal section and a distal section, the proximal section constructed out of a polymer material, the distal section constructed out of hardcoated aluminum.

24. The centrifugal pump of claim 19 wherein the stator comprises:
   a stator base shaped as a frustral cone with a trapezoidal cross-section along the central axis, the stator base having a maximum radial dimension and a minimum radial dimension, the maximum radial dimension defining the proximal end of the stator; and
   a spindle having first and second opposite ends aligned with the central axis, the first end attached to the minimum radial dimension of the lower section of the stator and the second end defining the distal end of the stator.

25. The centrifugal pump of claim 24 wherein the bearing is formed integral with the second end of the spindle.

26. The centrifugal pump of claim 19 wherein the bearing is a ball-shaped pivot bearing.

27. The centrifugal pump of claim 26 wherein the pivot bearing is hardcoated aluminum.

28. The centrifugal pump of claim 19 wherein the bearing is fixed to the distal end of the stator.

29. The centrifugal pump of claim 19 wherein the bearing is formed integral with the distal end of the stator.

30. The centrifugal pump of claim 19 wherein the bearing is fixed to the hub of the rotator at the central axis.

31. The centrifugal pump of claim 19 wherein the bearing is formed integral with the rotator at the central axis.

32. The centrifugal pump of claim 19 wherein the rotator is a generally conical-shaped impeller with a maximum radial end adjacent to the proximal end of the stator and a minimum radial end supported by the bearing.

33. The centrifugal pump of claim 19 wherein the rotator comprises a plurality of concentric cone-shaped rotators with maximal radial ends adjacent to the proximal end of the stator and with minimal radial ends supported by the bearing.

34. The centrifugal pump of claim 19 wherein the magnetic means comprises an annular magnetic ring having a plurality of magnetic poles.

35. The centrifugal pump of claim 19 wherein the magnetic means comprises a plurality of circumferentially spaced magnets.

36. The centrifugal pump of claim 19 wherein the magnetic means are positioned such that the magnetic lines of force are substantially directed toward the bearing and the central axis.

37. The centrifugal pump of claim 19 wherein the magnetic drive means comprises:
   a rotor positioned adjacent to the pump housing; and
   a plurality of drive magnets angularly spaced about the circumference of the rotor and oriented with the magnetic lines of force generated by the drive magnets aligning with the magnetic lines of force generated by the magnetic means carried by the rotator and intersecting the central axis such that resulting unbalanced forces on the rotator hub are substantially in a downward direction from the bearing at the distal end of the stator toward the proximal end of the stator, the resulting unbalanced forces being generally parallel to the central axis thereby stabilizing the rotation of the rotator about the bearing and the central axis.

38. A disposable pumping unit adapted to be releasably mounted on a magnetic drive means for pumping biological fluid such as blood, the pumping unit comprising:
   a pump housing having a pumping chamber therein, and an inlet and an outlet communicating with the pumping chamber;
   a bearing supported in the pumping chamber;
   an impeller positioned within the pumping chamber, the impeller having a hub rotatably supported on the bearing for rotation about an axis and having a plurality of openings configured to expose the bearing to the fluid; and
   magnetic means carried by the impeller within the pumping chamber adapted to be magnetically coupled with a magnetic drive means to rotate the impeller, and thereby pump fluid through the pumping unit.

39. A disposable pumping unit according to claim 38 wherein the bearing is supported generally adjacent the inlet for the flow of incoming fluid over the bearing.

40. A disposable pumping unit according to claim 39 wherein the bearing and the inlet are aligned along the axis of rotation of the impeller.

41. A disposable pumping unit according to claim 40 wherein the direction along the axis of rotation of the impeller from the bearing toward the inlet constitutes the upstream direction, the magnetic means forming magnetic lines of force intersecting the axis of rotation of the impeller upstream of the bearing.

42. A disposable pumping unit according to claim 40 wherein the magnetic means forms magnetic lines of force intersecting the bearing.

43. A disposable pumping unit adapted to pump biological fluid such as blood, the pumping unit comprising:
   a pump housing having a pumping chamber therein, and an inlet and an outlet communicating with the pumping chamber;
   a bearing supported in the pumping chamber;
   an impeller positioned within the pumping chamber, the impeller having a periphery, a plurality of radial blades which extend to the periphery and a hub which is rotatably supported on the bearing for rotation about an axis and is positioned between the inlet and the bearing, the radial blades defining a plurality of openings configured to expose the bearing to incoming fluid from the inlet;
   magnetic means carried by the impeller about the periphery and forming magnetic lines of force which intersect the axis of rotation of the impeller such that resulting balanced and unbalanced forces on the impeller stabilize rotation about the bearing and the axis.

44. The disposable pumping unit of claim 43 wherein a direction along the axis of rotation of the impeller from the bearing toward the inlet constitutes an upstream direction and wherein the magnetic lines of force intersect the axis of rotation of the impeller upstream from the bearing.

45. The disposable pumping unit of claim 43 wherein the magnetic lines of force intersect the axis of rotation of the impeller at the bearing.

* * * * *